United States Patent [19]
Krishnamurthy

[11] Patent Number: 5,811,126
[45] Date of Patent: Sep. 22, 1998

[54] CONTROLLED RELEASE MATRIX FOR PHARMACEUTICALS

[75] Inventor: Thinnayam N. Krishnamurthy, Ontario, Canada

[73] Assignee: Euro-Celtique, S.A., Luxembourg, Luxembourg

[21] Appl. No.: 537,392

[22] Filed: Oct. 2, 1995

[51] Int. Cl.$^6$ ............ A61K 9/16; A61K 9/58; A61K 9/22; A61K 47/06

[52] U.S. Cl. ............ 424/498; 424/487; 424/459; 424/468; 427/2.21; 427/212

[58] Field of Search ............ 242/484, 487, 242/459, 468, 470, 498, 501, 499; 427/2.21, 212

[56] References Cited

U.S. PATENT DOCUMENTS

| | | | |
|---|---|---|---|
| 3,108,046 | 10/1963 | Hardit | 167/82 |
| 4,235,870 | 11/1980 | Leslie | 424/458 |
| 4,401,456 | 8/1983 | Connick, Jr. | 424/488 |
| 4,717,713 | 1/1988 | Zatz et al. | 514/2 |
| 4,842,866 | 6/1989 | Horder | 424/468 |
| 4,861,598 | 8/1989 | Oshlack | 424/468 |
| 5,102,666 | 4/1992 | Acharya | 424/487 |
| 5,215,768 | 6/1993 | Krishamurthy | 424/488 |
| 5,229,128 | 7/1993 | Haddad et al. | 424/427 |
| 5,230,901 | 7/1993 | Einig et al. | 424/487 |

OTHER PUBLICATIONS

Abstract of Japanese Patent No. 1–163118 (A), entitled "Multi–Layer Suppository", Granted Jun. 27, 1989.

*Primary Examiner*—Edward J. Webman
*Attorney, Agent, or Firm*—Clifford M. Davidson

[57] ABSTRACT

A controlled release pharmaceutical composition for oral administration in humans or animals, comprising a controlled release matrix comprising a pharmaceutically acceptable sodium alginate, a pharmaceutically acceptable water swellable polymer, a pharmaceutically acceptable $C_2$–$C_{50}$ edible hydrocarbon derivative having a melting point ranging from 25° C. and 90° C. and a pharmaceutically acceptable divalent salt selected from the group consisting of an iron salt, a zinc salt, a magnesium salt, an aluminum salt and a calcium salt and mixtures of any of the foregoing and a therapeutically active agent to be administered and a lubricant or lubricants suitable for forming the composition into tablets or capsules and methods of making and using the same.

26 Claims, 5 Drawing Sheets

CONTROLLED RELEASE MATRIX FOR PHARMACEUTICALS

The present invention relates to a novel composition based upon a combination of an alginate, a divalent salt, a polymer and a long chain digestible hydrocarbon derivative, for providing a controlled release pharmaceutical composition and dosage form and methods for making and using the same.

BACKGROUND OF THE INVENTION

Controlled release pharmaceutical compositions and dosage forms designed to deliver substances, i.e., drugs, medicaments, active agents, diagnostic agents, or any substance to be internally administered to an animal, including humans, are used to improve the delivery of many such substances. A controlled release composition is typically used to improve the effects of administered substances by optimizing the kinetics of delivery of such an administered substance and thereby increasing patient compliance and convenience and also minimizing side effects associated with a high initial release rate and uneven blood or tissue levels.

Controlled-release of an orally administered substance, i.e., a drug, a medicament, an active agent, a diagnostic agent or any substance to be orally administered via the alimentary tract, maintains a desired concentration of the substance in the alimentary tract and/or the blood stream, for a longer duration than would occur if conventional rapid release dosage forms are administered.

Controlled-release formulations known in the art include specially coated pellets, coated tablets and capsules wherein a slow release of a drug is brought about through selective breakdown of the coating of the preparation or through compounding with a special matrix to affect the release of a drug. Some controlled-release formulations provide for sequential release of a single dose of an active compound at predetermined periods after administration.

Controlled-release preparations are designed to provide a longer period of pharmacologic or diagnostic response compared to conventional rapid release dosage forms. Such longer periods of response provide for many inherent benefits, e.g., therapeutic benefits, that are not achieved with corresponding short acting, immediate release preparations. For example, in the treatment of pain in patients in need of such treatment, controlled release formulations are useful to maintain relatively even analgesic release rates so that blood levels remain at a therapeutically effective level for a longer period of time.

The prior art teaching of the preparation and use of compositions providing for the controlled-release of an active compound from a carrier is basically concerned with the release of the active substance into the physiologic fluid of the alimentary tract. However, it is generally recognized that the mere presence of an active substance in the gastrointestinal fluids does not, by itself, insure bioavailability.

In order to be absorbed, the active drug substance must be in solution. The time required for a given proportion of an active substance from a unit dosage form is determined as the proportion of the amount of active drug substance released from a unit dosage form over a specified time base by a test method conducted under standardized conditions. The physiologic fluids of the gastrointestinal tract are the media for determining dissolution time. The present state of the art recognizes many satisfactory test procedures to measure dissolution time for pharmaceutical compositions, and these test procedures are described in official compendia world wide.

Although there are many diverse factors which influence the dissolution of drug substance from its carrier, the dissolution time determined for a pharmacologically active substance from the specific composition is relatively constant and reproducible. Among the different factors affecting the dissolution time are the surface area of the drug substance presented to the dissolution solvent medium, the pH of the solution, the solubility of the substance in the specific solvent medium, and the driving forces of the saturation concentration of dissolved materials in the solvent medium. Thus, the dissolution concentration of an active drug substance is dynamically modified in its steady state as components are removed from the dissolution medium through absorption across the tissue site. Under physiologic conditions, the saturation level of the dissolved materials is replenished from the dosage form reserve to maintain a relatively uniform and constant dissolution concentration in the solvent medium providing for a steady state absorption.

The transport across a tissue absorption site of the gastrointestinal tract is influenced by the Donnan osmotic equilibrium forces on both sides of the membrane since the direction of the driving force is the difference between the concentrations of active substance on either side of the membrane, i.e., the amount dissolved in the gastrointestinal fluids and the amount present in the blood. Since the blood levels are constantly being modified by dilution, circulatory changes, tissue storage, metabolic conversion and systemic excretion, the flow of active materials is directed from the gastrointestinal tract into the blood stream.

The absorption of a compound (e.g., a drug) is influenced by the degree of electrical charge borne by the compound at the absorption site, i.e., the ionization state of the compound. A compound in a non-ionized form more readily crosses the tissue absorption barrier than does a compound in an ionized state. Furthermore, the intrinsic oil-water partition coefficient for a compound which favors the oil phase, i.e., the lipophilicity of compound, is another characteristic promoting rapid absorption across the alimentary tract. These relationships are well established in the art through findings that absorbable materials must pass through a lipoid-like barrier when penetrating membranes at the absorption site.

Notwithstanding the diverse factors influencing both dissolution and absorption of a drug substance, a strong correlation has been established between the in vitro dissolution time determined for a dosage form and the in vivo bioavailability. This correlation is so firmly established in the art that dissolution time has become generally descriptive of bioavailability potential for the active component of the particular unit dosage composition. In view of this relationship, it is clear that the dissolution time determined for a composition is one of the important fundamental characteristics for consideration when evaluating slow release compositions.

Controlled-release pharmaceutical compositions for oral administration are generally known. Some controlled-release formulations are prepared from sodium alginate, which is the sodium salt of alginic acid, a purified carbohydrate obtained from brown seaweeds by extraction with dilute alkali. Other alginate salts are also known. For example, controlled release compositions consisting of a release matrix of sodium alginate and calcium salts are known. In addition, in vitro evaluations of floating alginate gel-systems consisting of sodium alginate, calcium phosphate, sodium bicarbonate, drug and diluent filled in a gelatin capsule have been reported. A method has also been described for treatment of diabetes by encapsulating islets of Langerhans in calcium alginate beads coated with a semipermeable membrane.

Acharya, 1992, discloses a calcium polycarbophil-alginate controlled-release composition in U.S. Pat. No. 5,110,605. Krishnamurthy, 1993, teaches a controlled-release suppository composition of sodium alginate and calcium salt, in U.S. Pat. No. 5,215,758, the disclosure of which is incorporated by reference herein in its entirety.

However, heretofore there has been no disclosure or teaching in the art of a solid alginate-based formulation including alginate, a water swellable polymer and a digestible hydrocarbon derivative, for providing an improved, prolonged and well-regulated controlled-release of orally administered compounds for a time period ranging from 6 hours up to 24 hours, or more, as compared to existing controlled-release alginate formulations.

OBJECTS AND SUMMARY OF THE INVENTION

It is accordingly an object of the present invention to provide a novel, solid, alginate-based controlled-release oral dosage form that is suitable for the oral administration of a drug incorporated in the dosage form for a time period ranging from about 6 to about 24 hours or more.

Another object of the present invention is to provide a novel, solid, alginate-based controlled-release oral dosage form which provides effective steady-state blood levels of an incorporated drug to be released in a patient for a time period ranging from about 6 to about 24 hours or more.

Still another object of the present invention is to provide a method of treating a patient with a novel, solid state, orally administrable dosage form of a which releases an incorporated drug over a prolonged period of time which provides a desired effect for a period from about 6 to about 24 hours or more, and which dosage form is bioavailable.

The present invention is related to the surprising discovery of a dosage form for the controlled-release of an orally administered substance, e.g., a drug having improved release characteristics. The dosage form according to the invention is a combination of a pharmaceutically acceptable alginate salt with a pharmaceutically acceptable water swellable polymer, a pharmaceutically acceptable $C_2$–$C_{50}$ edible hydrocarbon derivative having a melting point ranging from 25° C. and 90° C. and a pharmaceutically acceptable divalent salt such as an iron salt, a zinc salt, a magnesium salt, an aluminum salt and/or a calcium salt. These are combined with a therapeutically active agent to be administered and a lubricant or lubricants suitable for forming the composition into tablets or capsules.

The edible hydrocarbon derivative can be a higher aliphatic alcohol such as a fatty alcohol, substituted or unsubstituted, including, for example, cetyl alcohol, stearyl alcohol, cetostearyl alcohol and myristyl alcohol. The water swellable polymer can be a cellulose ether, substituted or unsubstituted, such as, for example, a hydroxyalkylcellulose and/or a carboxyalkylcellulose. For example, the cellulose ether can be hydroxyethylcellulose, hydroxypropylcellulose and/or hydroxypropylmethylcellulose.

Thus, in a preferred aspect, the invention provides, for example, a controlled release pharmaceutical composition for oral administration in humans or animals, including a controlled release matrix that includes a pharmaceutically acceptable sodium alginate, a pharmaceutically acceptable hydroxyalkylcellulose, a pharmaceutically acceptable higher aliphatic alcohol and a pharmaceutically acceptable calcium salt and mixtures of any of the foregoing and a therapeutically active agent to be administered and a lubricant or lubricants suitable for forming the composition into tablets or capsules.

In particular embodiments, the hydroxyethylcellulose ranges from about 3 to about 25% of the composition by weight; the sodium alginate ranges from about 10 to about 80% of the composition by weight; the calcium salt ranges from about 2 to about 12% by weight and the amount of higher aliphatic alcohol ranges from about 5% to about 45% by weight, all relative to sodium alginate. In a more particular embodiment, the hydroxyethylcellulose ranges from about 5 to about 18% of the composition by weight.

The sodium alginate has a viscosity from about 40 about 150 cps as a 1% solution or, more particularly, the sodium alginate has a viscosity ranging from about 300 to about 1000 cps as a 1% solution. The sodium alginate may also be described by its particle size, which will be in a range suitable for the preparation of the composition of the invention. In particular, the sodium alginate may have a particle size ranging from about 45 to about 200 microns. The sodium alginate has a mannuronic acid: guluronic acid ratio suitable for the preparation of the composition of the invention. This ratio includes a mannuronic acid: guluronic acid ratio about 0.40 to about 1.95.

Any suitable divalent calcium salt may be used in the composition, including calcium phosphate, dicalcium phosphate, calcium chloride, calcium carbonate, calcium acetate and calcium gluconate. The calcium salt can comprises from about 1 to about 6% by weight of the said composition.

A pharmaceutically acceptable higher alcohol component of the invention is preferably a $C_{12-36}$ fatty alcohol and more preferably may be a $C_{14}$–$C_{22}$ fatty alcohol, such as cetyl alcohol, stearyl alcohol, cetostearyl alcohol and/or myristyl alcohol. A fatty alcohol can make up from about 5% (w/w) to about 45% (w/w) by weight of the composition.

Any therapeutically active agent (drug) or diagnostic agent can be incorporated into the composition of the invention. Simply by way of example, a therapeutically active agent may be any of the following or even a combination of any of the following drugs: morphine, codeine, hydromorphone, oxycodone, oxybutynin, nicotine, amitriptyline, atropine, chlorpromazine, diclofenac, diphenhydramine, doxylamine, ephedrine, hyoscyamine, metoclopramide, papaverine, phenylpropanolamine, propranolol, quinidine, scopolamine, theophylline, tramadol and thioridazine.

The composition of the invention is produced, for example, by a process including the steps of mixing an active ingredient to be administered with hydroxyethylcellulose, sodium alginate, lactose and calcium salt to form a uniform mixture, hydrating the uniform mixture with water to form granules, drying the granules and coating the granules with a higher aliphatic alcohol. The process can also include the step of forming the granules into tablets or capsules.

BRIEF DESCRIPTION OF THE DRAWINGS

The following drawings are illustrative of certain embodiments of the invention and are not meant to limit the scope of the invention as encompassed by the claims.

DETAILED DESCRIPTION

Figure 1:
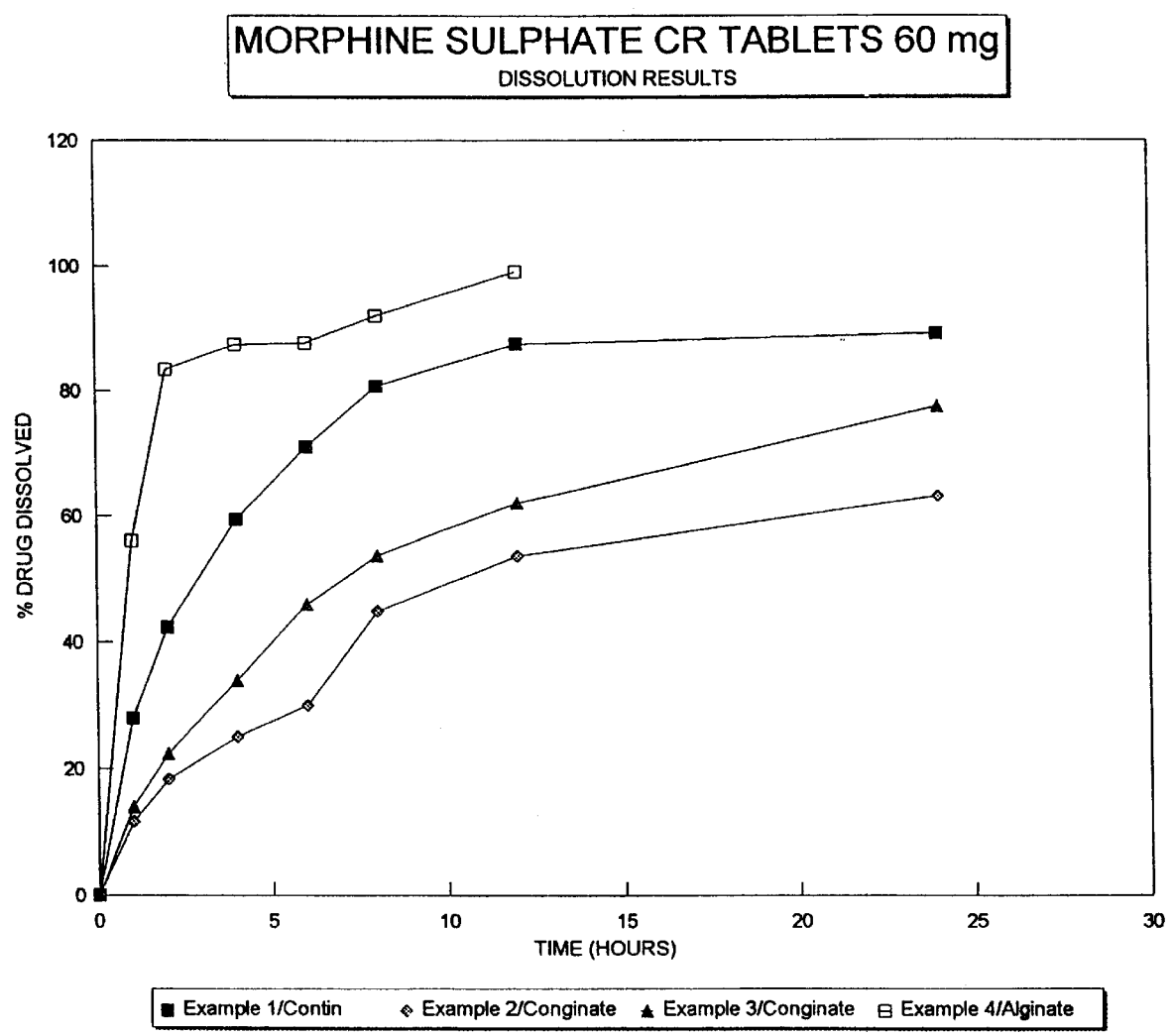
FIG. 1 is a graphical representation of the percent drug dissolved, verses time in hours, for the dissolution of tablets of the formulation including 60 mg morphine sulphate CR, obtained for Example 1, for Contin (■), Example 2, for Conginate (◇), Example 3, Conginate (▲) and Example 4, Alginate (□).

Accordingly, the present invention provides for novel compositions for providing controlled release pharmaceutical compositions and dosage forms for, e.g., oral administration. A composition according to the invention is provided, for example, as a matrix composed of: hydroxyalkylcellulose, sodium alginate, calcium salt, an effective amount of a water swellable polymer, a digestible hydrocarbon derivative and an effective amount of an active agent (e.g., a substance to be orally administered) distributed or suspended in the controlled release matrix, all of which are provided in a pharmaceutically acceptable form.

Without being bound by any particular hypothesis as to how the controlled release matrix according to the invention provides superior controlled release characteristics, upon oral ingestion and contact with fluids, the compositions of the present invention are believed to swell and gel to form a matrix from which the active ingredient (the drug) is released. Since the active ingredient is suspended or distributed throughout the composition and consequently throughout the matrix, a constant amount of active ingredient can be released per unit time in vivo by dispersion or erosion of the outer portions of the matrix.

In particular, it is believed that the polymer component, for example, the hydroxyalkylcellulose component, swells on contact with water. In addition, on contact with water, the divalent salt component, e.g., a calcium salt, cross-links with the sodium alginate to form a three-dimensional gel matrix, further slowing the dissolution of the composition. Further, an effective amount of a digestible hydrocarbon derivative, such as a higher aliphatic alcohol, provides an additional check on the dissolution of the composition and on the release rate of the active ingredient to be delivered.

Suitable materials for the controlled release composition or matrix include hydrophilic or hydrophobic polymers, such as gums, cellulose ethers and protein derived materials. Of these polymers, the cellulose ethers, especially hydroxyalkylcelluloses and carboxyalkylcelluloses, most especially hydroxyethylcellulose, hydroxypropylcellulose, hydroxypropylmethylcellulose, are preferred. The amount ranges from 3–25% and preferably from 5–18%.

Other suitable materials include digestible, long chain ($C_8$–$C_{50}$ and especially $C_8$–$C_{40}$) substituted or unsubstituted hydrocarbon derivatives, such as fatty acids, fatty alcohols, glyceryl esters of fatty acids, mineral oil and waxes. Preferably, the hydrocarbons derivatives have a melting point between 25° C. and 90° C. Of these, long chain hydrocarbon materials, fatty alcohols, and especially $C_{14}$–$C_{22}$ fatty alcohols, such as cetyl alcohol, stearyl alcohol, cetostearyl alcohol or myristyl alcohol are preferred.

The optimum concentration of, e.g., a higher aliphatic alcohol in the oral compositions of the present invention are determined by the rate of drug release required. Generally, the compositions contain from about 5% to about 45% (w/w), and preferably from about 10% to about 30% (w/w) of such a higher aliphatic alcohol, as a proportion to the weight of the composition. The greater the amount of higher aliphatic alcohol included in the matrix, the slower the rate of release of the drug.

Any alginates which are pharmaceutically acceptable can be used for the purpose of the present invention. Examples of commercially available alginates suitable for use in conjunction with the present invention are those that are marketed under the trade name Protanal and Keltone and are available from Protan A/S, Norway and Merck & Co. Inc., N.J., U.S.A., respectively.

Preferably, alginates having a viscosity range between 50–100 cps as a one percent solution in water are used. Most preferably, the alginate is a sodium alginate having a viscosity of from 300–1000 cps as a one percent solution or from about 40 to about 150 cps as a 1% solution. The sodium alginate has, for example, an M|G ratio (Mannuronic vs Guluronic acid) of 0.40 to 1.95 and more preferably has a ratio of 0.45 to 1.60.

The amount of alginate contained in the controlled release matrices and depends upon, e.g., the desired duration of action and the nature of the active drug substance to be incorporated into the composition. In general, the amount of alginate in the total composition ranges from about 10% to about 80% by weight. In certain embodiments the sodium alginate preferably ranges from about 10% to 50% by weight. Of course, the artisan will appreciate that the concentration of sodium alginate may be higher or lower depending upon the desired dosage regimen (i.e., the number of doses to be administered per day). Generally, the alginate particle size is any size suitable for forming the composition according to the invention. For example, preferred alginate particles sizes range from about 45 to about 200 microns.

The salts that may be used in the dosage form include any pharmaceutically acceptable divalent salts, including, for example, iron, zinc, aluminum, magnesium and calcium. Preferably, any pharmaceutically acceptable calcium salts known in the art may be used in the dosage form. Suitable calcium salts for use in the matrices and compositions of the invention include, for example, calcium phosphate, dicalcium phosphate, calcium chloride, calcium carbonate, calcium acetate and calcium gluconate.

The amount of divalent salt, e.g., calcium salt, must be sufficient to cross-link with the alginate when exposed to solution, such as gastric fluids, so that a gel matrix is formed from which the drug is slowly released. Generally, the concentration of calcium salt ranges from about 2 to about 12 percent, and more preferably from about 8 to 12 percent, by weight, relative to the amount of sodium alginate present in the composition.

Any pharmaceutically accepted soluble or insoluble inert pharmaceutical filler (diluent) material can be used in the compositions of the present invention, such as monosaccharides, disaccharides, polyhydric alcohols, or mixtures thereof. Examples of inert diluents include sucrose, dextrose, lactose, microcrystalline cellulose, xylitol, fructose, sorbitol, mixtures thereof and the like. However, it is preferred that a soluble pharmaceutical filler such as lactose, dextrose, sucrose, or mixtures thereof be used.

The solid dosage form according to the invention may be prepared in any suitable form for oral administration, including as a suspension or as a solid form. A solid form may be prepared as tablets, caplets or may be formed into a powder or beads suitable for delivery in a gelatin capsule.

In the case of tablets, an effective amount of any generally accepted pharmaceutical lubricant, including the calcium or magnesium stearate and talc, may be added to the above-mentioned ingredients at the time the active ingredient is added, or in any event prior to compression into a solid dosage form. Most preferred is magnesium stearate and talc in an amount of about 0.5–3% by weight of the solid dosage form.

The oral dosage form is prepared using any suitable process known to the art. Preferably, the dosage form is prepared by combining sodium alginate, calcium salt, hydroxyethylcellulose the active ingredient(s) and a higher aliphatic alcohol using a wet granulation technique of at least one step, to form a uniform granulate, together with any of the other excipients that are required for the tableting or the capsule filling.

Alternatively, the drug(s) can be combined during the process of preparing the granulate, or mixed with the granulate after it is prepared. The moist granulated mass with or without the drug(s) is then dried and sized using a suitable screening device to provide a flowable powder. The powder is then filled into capsules or compressed into matrix tablets or caplets, as desired.

The substances which may be used in the compositions of the present invention include any substances, either water soluble or water insoluble, which it is desirable to administer to a human or animal by a controlled release oral dosage form. Such substances include active drugs, prodrugs, proteins such as antibodies or enzymes, including digestive aids, vitamins, hormones. Substances that can be administered according to the invention also include diagnostic agents, including diagnostic antibodies (e.g., including antibodies for the detection of tumors), tracers such as radio-opaque or magnetic resonance imaging dyes and gastrointestinal absorption and motility tracers.

Examples of different classes of therapeutically active pharmaceutical agents that can be incorporated into the dosage form or matrices of the present invention include urinary incontinence agents (e.g., oxybutynin), antihistamines (e.g. dimenhydrinate, diphenhydramine (50–100 mg), chlorpheniramine and dexchlorpheniramine maleate), analgesics (e.g. aspirin, codeine, morphine (15–300 mg), dihydromorphone, oxycodone, etc.), anti-inflammatory agents (e.g. naproxyn, diclofenac, indomethacin, ibuprofen, acetaminophen, aspirin, sulindac), gastrointestinals and anti-emetics (e.g. metoclopramide (25–100 mg), anti-epileptics (e.g. phenytoin, meprobamate and nitrezepam), vasodilators (e.g. nifedipine, papaverine, diltiazem and nicardirine), anti-tussive agents and expectorants (e.g. codeine phosphate), anti-asthmatics (e.g. theophylline), anti-spasmodics (e.g. atropine, scopolamine), antismoking agents (e.g. nicotine), hormones (e.g. insulin, heparin), diuretics (e.g. eltacrymic acid bendrofluazide), anti-hypotensives (e.g. propranolol, clonidine), bronchodilators (e.g. albuterol), anti-inflammatory steroids (e.g. hydrocortisone, triamcinolone, prednisone), antibiotics (e.g., tetracycline), antihemorrhoidals, hypnotics, psychotropics, antidiarrheals, mucolytics, sedatives, decongestants, laxatives, antacids, vitamins, stimulants (including appetite suppressants such as phenylpropanolamine). GOODMAN AND GILMAN'S, THE PHARMACEUTICAL BASIS OF THERAPEUTICS, Eighth Edition, Eds, A. G. Gilman et al., Pergamon Press (1990), the disclosure of which is hereby incorporated herein by reference in its entirety.

EXAMPLES

The invention is further described in the following examples which are in no way intended to limit the scope of the invention.

EXAMPLES 1–4

Morphine Sulphate Controlled Release Tablets—60 mg

Morphine was tested in the controlled release system of the invention (Conginate system). The four formulations set forth in Table 1 exemplify a controlled release morphine tablet containing 60 mg active ingredient.

Preparation of Tablets

The tablets were prepared according to the following method. Morphine sulphate powder, hydroxyethylcellulose ("HEC"), sodium alginate, calcium chloride and lactose were dry mixed. The mixture was granulated with water until a wet granular mass was obtained. The granules were then dried in a Fluid Bed Dryer ("FBD") at 60° C. The dried material was sieved through a 12 mesh screen. The granulated material was warmed and added to molten cetostearyl alcohol (CSA) and the whole was mixed thoroughly.

The resulting mixture was allowed to cool in the air and then sieved through a 16 mesh screen. The coated granules were then lubricated with talc and magnesium stearate and compressed as round tablets. Dissolution experiments were then conducted using USP paddle method, 100 rpm, in 900 ml deionized water at 37° C. The results are set forth in Table 2 and FIG. 1.

Alternatively, the granulation can be done as follows. A substance to be delivered by controlled release, such as an active drug is charged, along with hydroxyethylcellulose, sodium alginate, calcium salt and lactose, into a fluid bed dryer. The mixture is fluidized for a few minutes and then water is sprayed water onto the FBD to obtain a granular mass. The granulate is then dried in the FBD. Molten CSA is then sprayed onto the granular mass and fluidized in the FBD. The coated granules are cooled, passed through a 16 mesh screen, and then lubricated with talc and/or magnesium stearate and compressed as tablets or filled into a gelatin capsule.

TABLE 1

MORPHINE SULPHATE CONTROLLED-RELEASE TABLETS
60 mg FORMULATIONS
Examples 1–4

| COMPONENTS | CONTIN Example 1 (mg/table) | CON-GINATE Example 2 (mg/table) | CON-GINATE Example 3 (mg/table) | ALGINATE Example 4 (mg/table) |
|---|---|---|---|---|
| Morphine Sulphate Pentahydrate | 60 | 60 | 60 | 60 |
| Hydroxyethylcellulose | 20 | 20 | 20 | — |
| Sodium Alginate | — | 75 | 50 | 100 |
| Calcium Chloride | — | 8 | 5 | 10 |
| Lactose | 140 | 57 | 85 | 70 |

TABLE 1-continued

MORPHINE SULPHATE CONTROLLED-RELEASE TABLETS
60 mg FORMULATIONS
Examples 1–4

| COMPONENTS | CONTIN Example 1 (mg/table) | CON-GINATE Example 2 (mg/table) | CON-GINATE Example 3 (mg/table) | ALGINATE Example 4 (mg/table) |
|---|---|---|---|---|
| Cetostearyl alcohol | 70 | 70 | 70 | 50 |
| Talc | 5 | 5 | 5 | 5 |
| Magnesium stearate | 5 | 5 | 5 | 5 |
| Total Weight/Tablet | 300 | 300 | 300 | 300 |

TABLE 2

MORPHINE SULPHATE CONTROLLED-RELEASE
TABLETS 60 mg FORMULATIONS

% MORPHINE SULPHATE PENTAHYDRATE DISSOLVED

| HOUR | CONTIN Example 1 (mg/tablet) | CONGINATE Example 2 (mg/tablet) | CONGINATE Example 3 (mg/tablet) | ALGINATE Example 4 (mg/tablet) |
|---|---|---|---|---|
| 1 | 27.9 | 11.6 | 13.9 | 56.1 |
| 2 | 42.3 | 18.3 | 22.4 | 83.4 |
| 4 | 59.5 | 25.0 | 34.0 | 87.4 |
| 6 | 71.1 | 30.0 | 46.0 | 87.6 |
| 8 | 80.8 | 44.9 | 53.8 | 92.0 |
| 12 | 87.5 | 53.7 | 62.1 | 99.0 |
| 24 | 89.1 | 63.3 | 77.6 | — |

In Example 1, no alginate was used. The formula represents the typical CONTIN-type composition (CONTIN is a trademark of Purdue Frederick for controlled release morphine sulphate) comprising, in addition to morphine sulphate, cetostearyl alcohol, hydroxyethyl cellulose, hydroxypropyl methylcellulose, lactose, magnesium stearate, talc and coloring agents). The amount of hydroxyethylcellulose was about 6.7%, the amount of cetostearyl alcohol was about 23.3% by weight of the composition, respectively.

In Example 2, in addition to the CONTIN ingredients, sodium alginate and calcium chloride were added (the Conginate System). The amount of alginate was about 25%, the amount of calcium salt was about 2.7% by weight of the composition.

In Example 3, the amount of alginate was about 16.7%, the amount of calcium salt about 1.67%, by weight of the composition.

In Example 4, the CONTIN ingredients were omitted. The formulation included about 33.3% alginate and about 3.3% of calcium salt, by weight of the composition.

Discussion

From the dissolution results (Table 2 and FIG. 1) it can be seen that the release obtained from the Conginate System is much more sustained than the alginate of Example 4 or the CONTIN System. By varying the amount of alginate, the dissolution rate can be adjusted and the release of morphine sulfate can be extended, e.g. up to 24 hours or further.

EXAMPLES 5–7

Morphine Sulphate Controlled Release Tablets: 30, 60 & 100 mg
Varying Amount of Drug In Examples 5–7, controlled release morphine sulphate tablets were prepared in which the amount of drug in 30, 60 and 100 mg, respectively. The tablet formulations set forth in Table 3 were prepared using the method described by Examples 1–4, above.

TABLE 3

MORPHINE SULPHATE CONTROLLED-RELEASE TABLETS:
30, 60 & 100 mg FORMULATIONS
Examples 5–7

| COMPONENTS | Example 5 (mg/tablet) | Example 6 (mg/tablet) | Example 7 (mg/tablet) |
|---|---|---|---|
| Morphine Sulphate Pentahydrate | 30 | 60 | 100 |
| Hydroxyethylcellulose | 15 | 20 | 20 |
| Sodium Alginate | 50 | 50 | 50 |
| Calcium Chloride | 5 | 5 | 5 |
| Lactose | 60 | 20 | — |
| Cetostearyl alcohol | 35 | 40 | 40 |
| Talc | 3 | 3 | 3 |
| Magnesium stearate | 2 | 2 | 2 |
| Total Weight/Tablet | 200 | 200 | 220 |

In Example 5, the composition included 25% alginate, 2.5% calcium salt, 7.5% HEC and 17.5% CSA.

In Example 6, the composition included 25% alginate, 2.5% calcium salt, 10% HEC and 20% CSA.

In Example 7, the composition included 22.7% alginate, 2.27% calcium salt, 9.1% HEC and 18.2% CSA.

Figure 2:
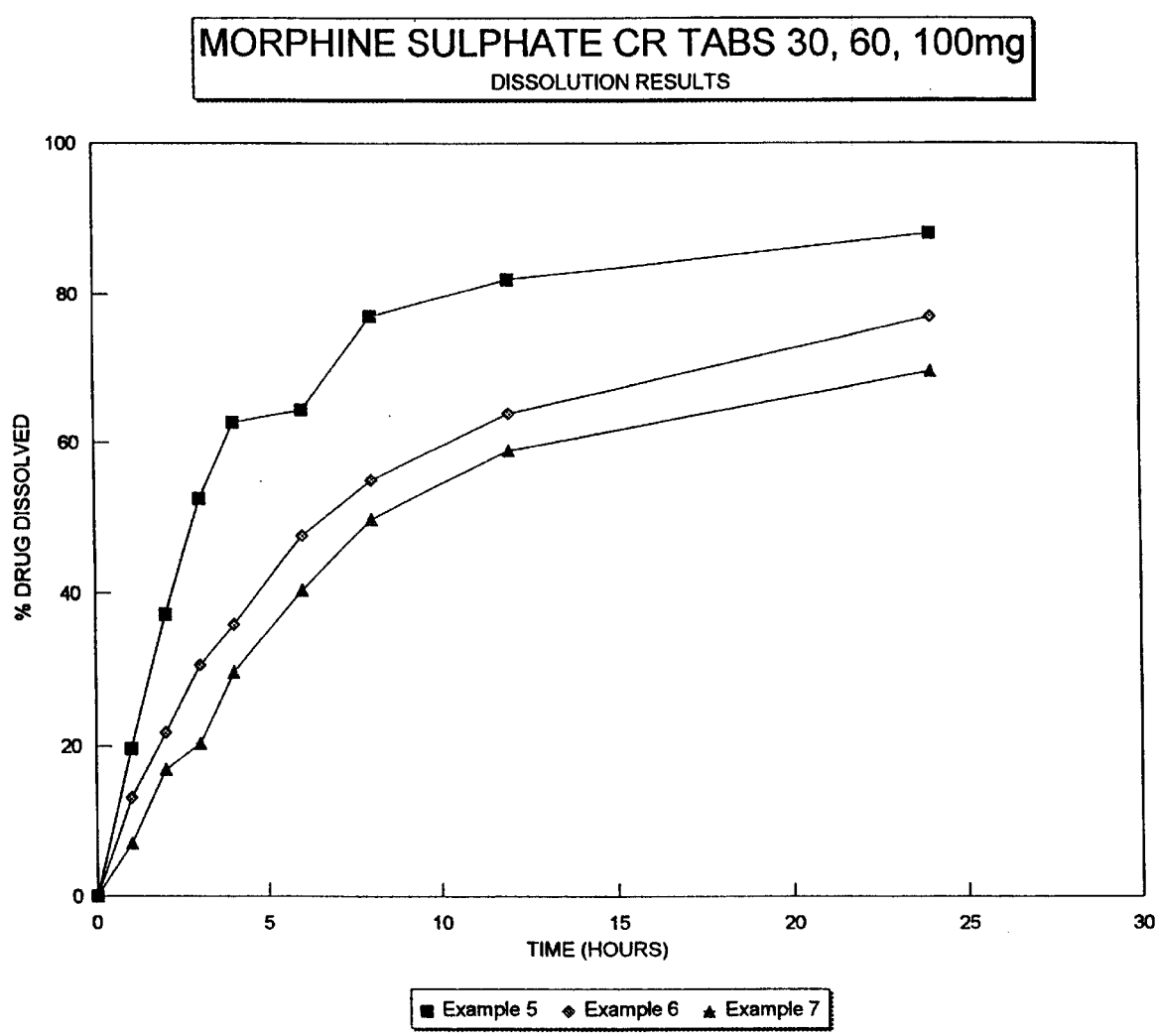
FIG. 2 is a graphical representation of the percent drug dissolved, verses time in hours, for the dissolution of tablets of the formulation including 30, 60 and 100 mg of morphine sulphate CR, obtained for Example 5 (■), Example 6 (◊) and Example 7(▲).

The tablets were then tested for dissolution using USP paddle method, 100 rpm in deionized water for 24 hours. The dissolution results are set forth in Table 4 and FIG. 2.

TABLE 4

MORPHINE SULPHATE CONTROLLED-RELEASE TABLETS:
30, 60 & 100 mg FORMULATIONS: DISSOLUTION RESULTS
Examples 5–7

| | % MORPHINE SULPHATE PENTAHYDRATE | | |
|---|---|---|---|
| HOUR | Example 5 | Example 6 | Example 7 |
| 1 | 19.7 | 13.2 | 7.2 |
| 2 | 37.2 | 21.8 | 17.0 |
| 3 | 52.5 | 30.5 | 20.4 |
| 4 | 62.7 | 35.9 | 29.6 |
| 6 | 64.4 | 47.6 | 40.4 |
| 8 | 77.0 | 55.0 | 49.8 |
| 12 | 82.0 | 64.0 | 59.0 |
| 24 | 88.0 | 77.0 | 69.7 |

Discussion

Thus, different strengths of morphine sulphate tablets with controlled release characteristics can be manufactured by varying the proportions of the different ingredients in the controlled release Conginate system of the present invention. In particular, Example 7 provides the most prolonged release, so that 69.7% morphine sulphate was released at 24 hours.

EXAMPLES 8–10

Nicotine Bitartrate Controlled Release Tablets: 100 mg

An oral controlled release composition according to the present invention was prepared with the formulation set forth in Table 5, each containing 100 mg of nicotine bitartrate (a highly soluble drug) using the method described by Examples 1–4, above.

TABLE 5

NICOTINE BITARTRATE CONTROLLED-RELEASE TABLETS - 100 mg FORMULATIONS
Examples 8–10

| COMPONENTS | Example 8 | Example 9 | Example 10 |
|---|---|---|---|
| Nicotine Bitartrate dihydrate | 100 | 100 | 100 |
| Hydroxyethylcellulose | 30 | 30 | — |
| Sodium Alginate | — | 50 | 75 |
| Calcium Chloride | — | 5 | 8 |
| Lactose | 125 | 85 | 72 |
| Cetostearyl alcohol | 60 | 45 | 60 |
| Talc | 5 | 5 | 5 |
| Magnesium stearate | 5 | 5 | 5 |
| Total Weight/Tablet | 325 | 325 | 325 |

In Example 8, no alginate was used. The amount of HEC was 9.2%, CSA was 18.5%.

In Example 9, the Conginate system (the present invention), the composition included 9.2%, 15.4% alginate, 1.54% calcium salt and 13.8% CSA.

In Example 10, only sodium alginate (23.1%) and calcium chloride (~2.5%) by weight of the composition were used.

Figure 3:
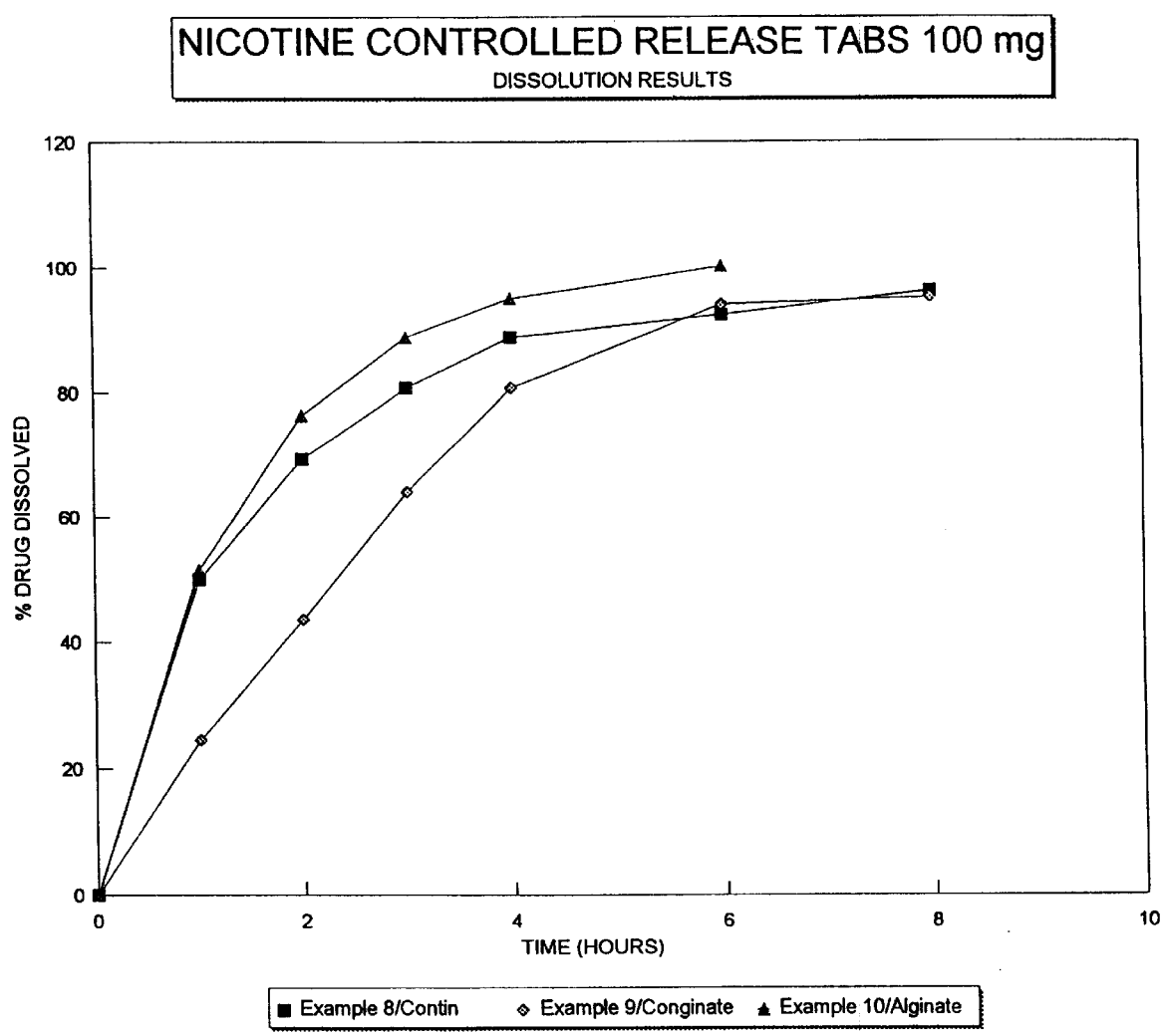
FIG. 3 is a graphical representation of the percent drug dissolved, verses time in hours, for the dissolution of tablets of the formulation, including 100 mg nicotine, obtained for Example 8, Contin (■), Example 9, Conginate (◊) and Example 10, Alginate (▲).

The compressed tablets were tested for dissolution using the USP basket method at 100 rpm, in 900 ml deionized water, at 37° C. The results are set forth in Table 6 and FIG. 3.

TABLE 6

NICOTINE BITARTRATE CONTROLLED-RELEASE TABLETS - 100 mg DISSOLUTION RESULTS
Examples 8–10

% NICOTINE BITARTRATE DISSOLVED

| HOUR | CONTIN Example 8 | CONGINATE Example 9 | ALGINATE Example 10 |
|---|---|---|---|
| 1 | 50.0 | 24.6 | 51.5 |
| 2 | 69.3 | 43.6 | 76.4 |
| 3 | 80.8 | 64.0 | 88.8 |
| 4 | 88.8 | 80.8 | 95.0 |
| 6 | 92.4 | 94.0 | 100.2 |
| 8 | 96.2 | 95.2 | — |

Discussion

Example 9, provided the most prolonged release of nicotine and confirm that the formulation of the invention has superior controlled release characteristics compared to either of the other two systems, namely CONTIN and alginate, even for highly soluble drugs.

EXAMPLES 11–14

Oxybutynin Controlled Release Tablets—20 mg

The method of Examples 8–10 was repeated with yet another highly soluble drug, oxybutynin chloride. The compositions for the controlled release tablets are given in Table 7 as Examples 11, 12, 13 and 14.

TABLE 7

OXYBUTYNIN CONTROLLED RELEASE TABLETS: 20 mg FORMULATIONS
Examples 11–14

| COMPONENTS | CONGINATE Example 11 (mg/table) | CONGINATE Example 12 (mg/table) | CONTIN Example 13 (mg/table) | ALGINATE Example 14 (mg/table) |
|---|---|---|---|---|
| Oxybutynin chloride | 20 | 20 | 20 | 20 |
| Hydroxyethylcellulose | 20 | 30 | 20 | — |
| Sodium Alginate (Keltone HVCR) | 30 | 50 | — | 30 |
| Calcium Chloride | 3 | 5 | — | 3 |
| Lactose | 96 | 49 | 129 | 116 |
| Cetostearyl alcohol | 30 | 45 | 30 | 30 |
| Magnesium stearate | 1 | 1 | 1 | 1 |
| Total Weight/Tablet | 200 | 200 | 200 | 200 |

In Example 11, the composition included 10% HEC, 15% alginate, 1.5% calcium salt and 15% CSA.

In Example 12, the composition included 15% HEC, 25% alginate, 2.5% calcium salt and 22.5% CSA.

In Example 13, the composition included 10% HEC and 15% CSA. In Example 14, the composition included 15% alginate, 1.5% calcium salt and 15% CSA.

Figure 4:
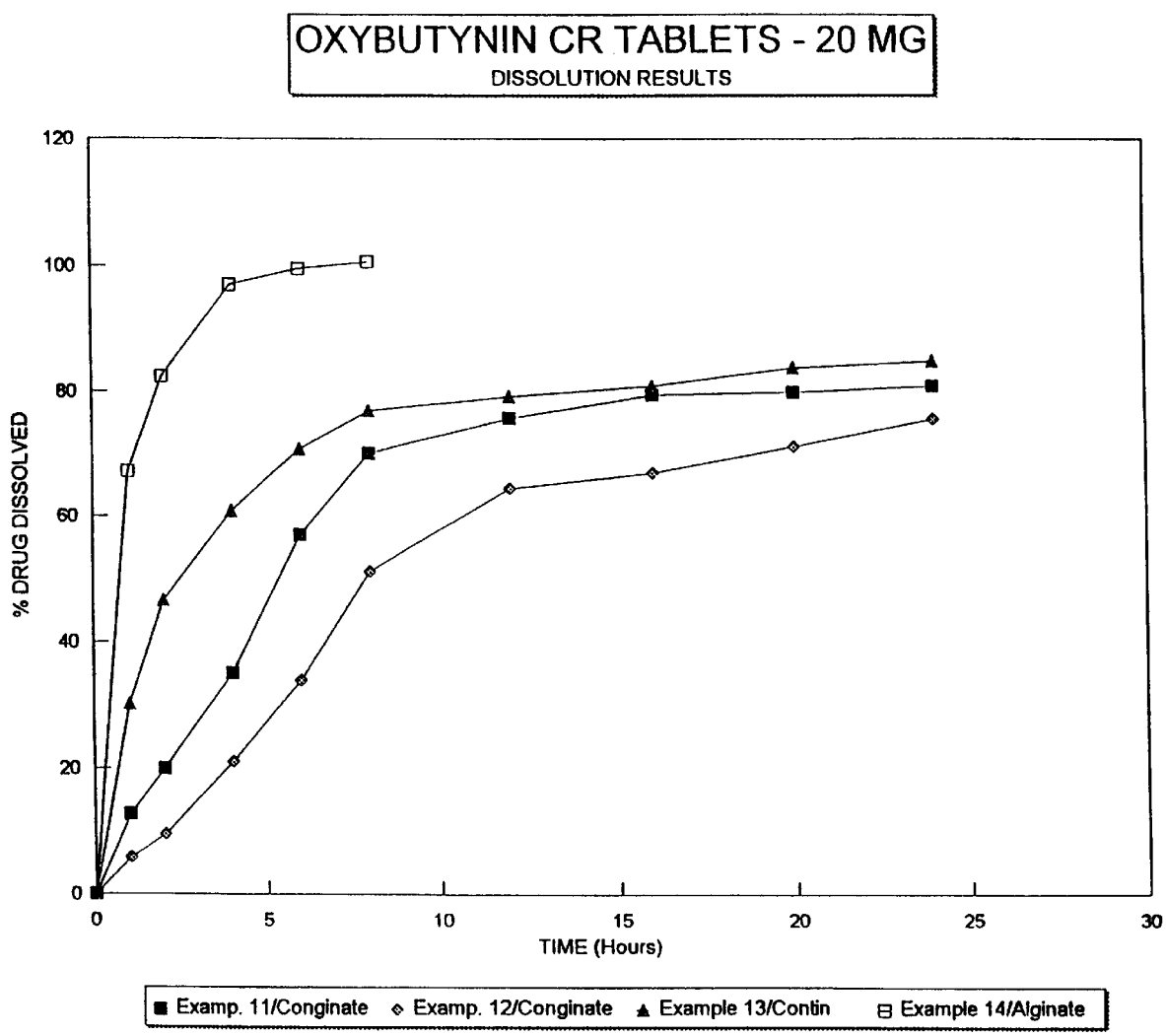
FIG. 4 is a graphical representation of the percent drug dissolved, verses time in hours, for the dissolution of tablets of the formulation including 20 mg of oxybutynin CR, obtained for Example 11, Conginate (■), Example 12, Conginate (◊), Example 13, Contin (▲) and Example 14, Alginate (□).

The dissolution profile of the tablets, shown in Examples 11–14, were conducted using the USP paddle method at 100 rpm, in 900 mL of water at 37° C. The results are summarized in Table 8 and FIG. 4.

TABLE 8

OXYBUTYNIN CONTROLLED RELEASE TABLETS - 20 mg DISSOLUTION RESULTS
Examples 11–14

% OXYBUTYNIN CHLORIDE DISSOLVED

| HOUR | CONGINATE Example 11 | CONGINATE Example 12 | CONTIN Example 13 | ALGINATE Example 14 |
|---|---|---|---|---|
| 1 | 12.9 | 6.0 | 30.2 | 67.1 |
| 2 | 20.0 | 9.8 | 46.5 | 82.5 |
| 4 | 35.0 | 21.1 | 60.8 | 96.9 |
| 6 | 57.0 | 34.0 | 70.7 | 99.5 |

TABLE 8-continued

OXYBUTYNIN CONTROLLED RELEASE TABLETS - 20 mg
DISSOLUTION RESULTS
Examples 11–14

% OXYBUTYNIN CHLORIDE DISSOLVED

| HOUR | CONGINATE Example 11 | CONGINATE Example 12 | CONTIN Example 13 | ALGINATE Example 14 |
|---|---|---|---|---|
| 8  | 70.1 | 51.2 | 77.0 | 100.6 |
| 12 | 75.8 | 64.5 | 79.3 | —     |
| 16 | 79.6 | 67.0 | 81.0 | —     |
| 20 | 80.0 | 71.2 | 84.0 | —     |
| 24 | 81.0 | 75.7 | 85.0 | —     |

Discussion

Examples 11 and 12 confirm that the Conginate system provided the most prolonged release, i.e. only 81% and 75.7% release, respectively, at 24 hours compared to 85% release for CONTIN and 100% release (at 8 hours) for alginate.

EXAMPLES 15–17

Oxybutynin Controlled Release Tablets—15 mg

Varying amount of drug

In examples 15–17, a series of controlled-release oxybutynin chloride tablets with 15 mg active drug per tablet, were prepared as shown in Table 9. The tablet formulations set forth in Table 9 were prepared using the method of Examples 1–4, above.

TABLE 9

OXYBUTYNIN CONTROLLED RELEASE TABLETS -
15 mg FORMULATIONS
Examples 15–17

| COMPONENTS | Example 15 | Example 16 | Example 17 |
|---|---|---|---|
| Oxybutynin chloride | 15.0 | 15.0 | 15.0 |
| Hydroxyethylcellulose | 15.0 | 15.0 | 22.50 |
| Sodium Alginate (Keltone HVCR) | 7.50 | 15.0 | 67.50 |
| Calcium Chloride | 0.75 | 1.50 | 6.75 |
| Lactose | 84.75 | 64.0 | 11.25 |
| Cetostearyl alcohol | 22.50 | 35.00 | 22.50 |
| Talc | 2.25 | 2.25 | 2.25 |
| Magnesium stearate | 1.25 | 2.25 | 2.25 |
| Total Weight/Tablet | 150 | 150 | 150 |

In Example 15, the composition included 10% HEC, 5% alginate, 0.5% calcium salt, and 15% CSA.

In Example 16, the composition included 10% HEC, 23.3% CSA, 10% alginate and 1% calcium salt.

In Example 17, the composition included 1.5% HEC, 15% CSA, 4.5% alginate and 4.5% calcium salt.

Figure 5:
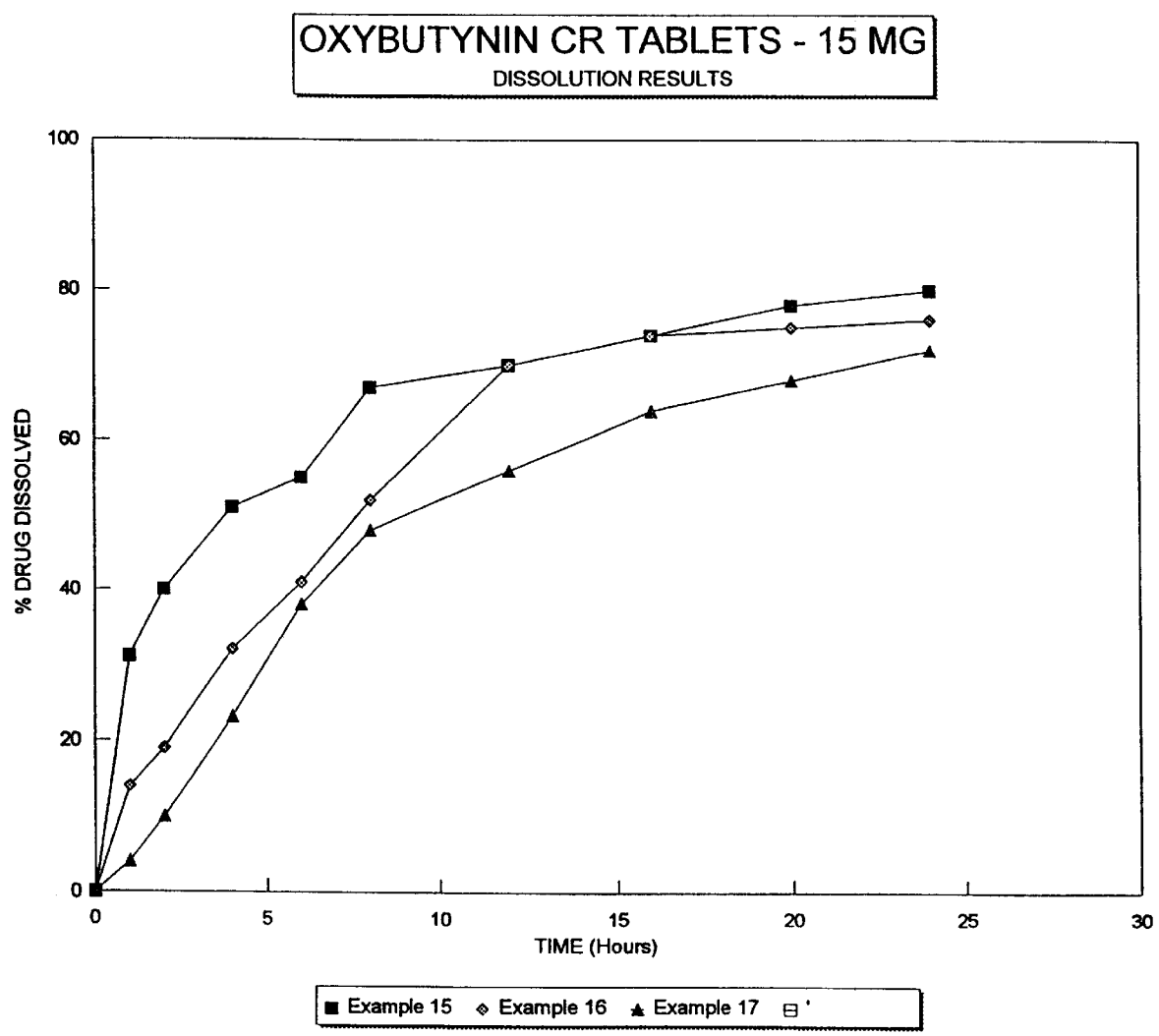
FIG. 5 is a graphical representation of the percent drug dissolved, verses time in hours, for the dissolution of tablets of the formulation including 15 mg of oxybutynin CR, obtained for Example 15 (■), Example 16 (◊), Example 17 (□).

The dissolution release rate of the formulae in Table 9 are reported in Table 10 and FIG. 5.

TABLE 10

OXYBUTYNIN CONTROLLED RELEASE TABLET - 15 mg
DISSOLUTION RESULTS
Examples 15–17

% OXYBUTYNIN CHLORIDE RELEASED

| HOUR | Example 15 | Example 16 | Example 17 |
|---|---|---|---|
| 1  | 31 | 14 | 4  |
| 2  | 40 | 19 | 10 |
| 4  | 51 | 32 | 23 |
| 6  | 55 | 41 | 38 |
| 8  | 67 | 52 | 48 |
| 12 | 70 | 70 | 56 |
| 16 | 74 | 74 | 64 |
| 20 | 78 | 75 | 68 |
| 24 | 80 | 76 | 72 |

Discussion

Comparison of Examples 15, 16 and 17 confirms the release-prolonging effect of additional alginate in the formulation of the invention. Thus, Example 17, with 67.50 mg/tablet sodium alginate, provided a lower release rate than the other two formulations throughout the test period.

EXAMPLES 18–19

Oxybutynin Controlled Release Tablets: 15 mg
Effect of M|G Ratio

Two types of alginates, having different Mannuronic acid/Guluronic acid were used in preparing the oxybutynin CR 15 mg tablets, Protanal SF 200, having an M|G ratio of ~0.45 and Keltone HV, having an M|G ratio of ~1.56 were used in preparing formulations set forth in Examples 18 and 19.

TABLE 11

OXYBUTYNIN CONTROLLED RELEASE TABLETS - 15 mg
FORMULATIONS
Examples 18 and 19

| COMPONENTS | Example 18 (mg/tablet) | Example 19 (mg/tablet) |
|---|---|---|
| Oxybutynin chloride | 15 | 15 |
| Hydroxyethylcellulose | 15 | 15 |
| Protanal SF 200 | 15 | — |
| Sodium Alginate (Keltone HVCR) | — | 15 |
| Calcium Phosphate Dibasic | 1.5 | 1.5 |
| Cetostearyl alcohol | 35 | 35 |
| Lactose | 63.5 | 63.5 |
| Talc | 2.5 | 2.5 |
| Magnesium stearate | 2.5 | 2.5 |
| Total Weight/Tablet | 150 | 150 |

TABLE 12

OXYBUTYNIN CONTROLLED RELEASE TABLETS - 15 mg
DISSOLUTION RESULTS
Examples 18 and 19

% OXYBUTYNIN CHLORIDE RELEASED

| HOUR | Example 18 | Example 19 |
|---|---|---|
| 1 | 5.9  | 4.6  |
| 2 | 12.5 | 10.9 |
| 4 | 14.8 | 15.3 |

TABLE 12-continued

OXYBUTYNIN CONTROLLED RELEASE TABLETS - 15 mg
DISSOLUTION RESULTS
Examples 18 and 19

% OXYBUTYNIN CHLORIDE RELEASED

| HOUR | Example 18 | Example 19 |
|---|---|---|
| 6 | 21.2 | 20.5 |
| 8 | 30.5 | 31.5 |
| 12 | 48.5 | 49.9 |
| 18 | 58.4 | 58.2 |
| 24 | 59.7 | 60.7 |

Discussion

The dissolution profile of the above two formulations were evaluated and the results obtained are shown in Table 12. The dissolution test was carried out at pH 7.4, in phosphate buffer at 37° C., using the USP paddle method at 100 rpm. Both types of alginates are capable of producing an extended release of active ingredients.

CONCLUSION

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

What is claimed is:

1. A controlled release pharmaceutical composition for oral administration in humans or animals, comprising
a controlled release matrix comprising from about 10 to about 80% of the composition by weight of a pharmaceutically acceptable sodium alginate, from about 3 to about 25% of the composition by weight of a pharmaceutically acceptable water swellable polymer, from about 5 to about 45% of the composition by weight a pharmaceutically acceptable $C_2$–$C_{50}$ edible hydrocarbon derivative having a melting point ranging from 25° C. to 90° C. and a pharmaceutically acceptable divalent salt sufficient to cross-link with the alginate and selected from the group consisting of an iron salt, a zinc salt, a magnesium salt, an aluminum salt and a calcium salt and mixtures of any of the foregoing, with
a therapeutically effective amount of the active agent to be administered.

2. The composition according to claim 1 wherein the edible hydrocarbon derivative is a higher aliphatic alcohol.

3. The composition according to claim 2 wherein the higher aliphatic alcohol is selected from the group consisting of cetyl alcohol, stearyl alcohol, cetostearyl alcohol and myristyl alcohol.

4. The composition according to claim 1 wherein the water swellable polymer is a cellulose ether.

5. The composition according to claim 4 wherein the cellulose ether is selected from the group consisting of a hydroxyalkylcellulose, and a carboxyalkylcellulose.

6. The composition according to claim 4 wherein the cellulose ether is selected from the group consisting of hydroxyethylcellulose, hydroxypropylcellulose and hydroxypropylmethylcellulose.

7. A controlled release pharmaceutical composition for oral administration in humans or animals, comprising
a controlled release matrix comprising a pharmaceutically acceptable sodium alginate in an amount from about 10 to about 80% of said composition by weight, a pharmaceutically acceptable hydroxylalkylcellulose in an amount from about 3 to about 25% of said composition by weight, a pharmaceutically acceptable higher aliphatic alcohol containing from 2 to 50 carbon atoms in an amount from about 5 to about 45% of said composition by weight, and a pharmaceutically acceptable calcium salt in an amount from about 2 to about 12% by weight of the sodium alginate in said composition and,
a therapeutically effective amount of the active agent to be administered.

8. The controlled release composition according to claim 7 in tablet form.

9. The composition according to claim 8 comprising an effective amount of a drug selected from the group consisting of morphine and salts thereof.

10. The controlled release composition according to claim 7 in capsule form.

11. The composition according to claim 8 comprising an effective amount of a drug selected from the group consisting of nicotine and salts thereof.

12. The composition of claim 7, wherein the sodium alginate has a viscosity from about 40 about 150 cps as a 1% solution.

13. The composition of claim 7 wherein the sodium alginate has a viscosity from about 300 to about 1000 cps as a 1% solution.

14. The composition of claim 7, wherein the sodium alginate has a particle size from about 45 to about 200 microns.

15. The composition of claim 7, wherein the sodium alginate has a mannuronic acid: guluronic acid ratio about 0.40 to about 1.95.

16. The composition of claim 7, wherein the calcium salt is selected from the group consisting of calcium phosphate, dicalcium phosphate, calcium chloride, calcium carbonate, calcium acetate and calcium gluconate.

17. The composition of claim 7, wherein the calcium salt comprises from about 1 to about 6% by weight of the composition.

18. The composition of claim 7, wherein the higher aliphatic alcohol comprises a $C_{12-36}$ fatty alcohol.

19. The composition according to claim 7 wherein the higher aliphatic alcohol comprises a $C_{14}$–$C_{22}$ fatty alcohol.

20. A composition according to claim 7 wherein the higher aliphatic alcohol is selected from the group consisting of cetyl alcohol, stearyl alcohol, cetostearyl alcohol and myristyl alcohol.

21. The composition according to claim 19, wherein the amount of fatty alcohol comprises about 5% by weight of the composition to about 45% (w/w) by weight of the composition.

22. The composition of claim 7, wherein said therapeutically active agent is selected from the group consisting of morphine, codeine, hydromorphone, oxycodone, oxybutynin, nicotine, amitriptyline, atropine, chlorpromazine, diclofenac, diphenhydramine, doxylamine, ephedrine, hyoscyamine, metoclopramide, papaverine, phenyl-propanolamine, propranolol quinidine, scopolamine, theophylline, tramadol and thioridazine.

23. A process for producing a controlled release composition for oral administration comprising
mixing a therapeutically effective amount of an active ingredient to be administered into a controlled release matrix comprising a pharmaceutically acceptable hydroxyethylcellulose in an amount of about 3 to about 25% of said composition by weight, a pharmaceutically acceptable sodium alginate in an amount from about 10 to about 80% of said composition by weight, lactose and a pharmaceutically acceptable calcium salt in an amount from about 2 to about 12% by weight of the composition to form a uniform mixture, hydrating the uniform mixture with water to form granules, drying the granules and coating the granules with said higher aliphatic alcohol.

24. The composition according to claim 8 comprising an effective amount of a drug selected from the group consisting of oxybutynin and salts thereof.

25. The composition according to claim 7 further comprising a lubricant present in a weight percent ranging from about 0.5 to about 3 percent of the composition.

26. The process of claim 23 further comprising the step of forming said granules into tablets or capsules.

* * * * *